US011986283B2

(12) United States Patent
Peltonen et al.

(10) Patent No.: US 11,986,283 B2
(45) Date of Patent: May 21, 2024

(54) METHODS AND APPARATUS FOR COUGH DETECTION IN BACKGROUND NOISE ENVIRONMENTS

(71) Applicant: RESAPP HEALTH LIMITED, Red Hill (AU)

(72) Inventors: Vesa Tuomas Kristian Peltonen, Red Hill (AU); Anthony James Keating, Red Hill (AU); Nicholas Kim Partridge, Red Hill (AU)

(*) Notice: Subject to any disclaimer, the term of this patent is extended or adjusted under 35 U.S.C. 154(b) by 994 days.

(21) Appl. No.: 16/483,013

(22) PCT Filed: Feb. 1, 2018

(86) PCT No.: PCT/AU2018/050062
§ 371 (c)(1),
(2) Date: Aug. 1, 2019

(87) PCT Pub. No.: WO2018/141013
PCT Pub. Date: Aug. 9, 2018

(65) Prior Publication Data
US 2020/0015709 A1 Jan. 16, 2020

(30) Foreign Application Priority Data

Feb. 1, 2017 (AU) .................. 2017900300
Jun. 8, 2017 (AU) .................. 2017902184

(51) Int. Cl.
*A61B 5/08* (2006.01)
*A61B 5/00* (2006.01)
*G06N 3/045* (2023.01)

(52) U.S. Cl.
CPC .......... *A61B 5/0823* (2013.01); *A61B 5/7203* (2013.01); *A61B 5/7267* (2013.01); *G06N 3/045* (2023.01)

(58) Field of Classification Search
CPC ... A61B 5/0823; A61B 5/7203; A61B 5/7267; G06N 3/0454
See application file for complete search history.

(56) References Cited

U.S. PATENT DOCUMENTS

| 8,411,977 B1 | 4/2013 | Baluja et al. |
| 2005/0119586 A1 | 6/2005 | Coyle et al. |

(Continued)

FOREIGN PATENT DOCUMENTS

| JP | 07-000376 A | 1/1995 |
| JP | 2007-327993 A | 12/2007 |

(Continued)

OTHER PUBLICATIONS

Barry, Samantha J., et al., "The automatic recognition and counting of cough," Cough, Biomed Central, London, GB, vol. 2, No. 1, Sep. 28, 2006 (Year: 2006).*

(Continued)

*Primary Examiner* — Robert J Michaud

(57) ABSTRACT

A method for detecting cough sounds from a sound wave of a subject includes applying features extracted from the sound wave to at least two electronic pattern classifiers including a first classifier trained to detect an explosive phase of a cough and a second classifier trained to detect one or more post-explosive phases of the cough sound. The features extracted from the sound wave are applied to the second classifier after the first classifier has classified features of the sound wave as an explosive phase of a cough sound.

20 Claims, 16 Drawing Sheets

(56) References Cited

U.S. PATENT DOCUMENTS

| | | |
|---|---|---|
| 2011/0087079 A1 | 4/2011 | Aarts |
| 2014/0336537 A1* | 11/2014 | Patel .................... A61B 5/0816 |
| | | 600/586 |
| 2015/0073306 A1* | 3/2015 | Abeyratne ............. A61B 5/742 |
| | | 600/586 |
| 2016/0345893 A1 | 12/2016 | Von Janecek et al. |
| 2019/0088367 A1* | 3/2019 | Stamatopoulos ...... G16H 10/60 |

FOREIGN PATENT DOCUMENTS

| | | |
|---|---|---|
| JP | 2009-532072 A | 9/2009 |
| WO | WO 2006/002338 A2 | 2/2006 |
| WO | WO 2013/142908 A1 | 10/2013 |
| WO | WO 2017/032873 A2 | 3/2017 |
| WO | WO 2018/141013 A2 | 8/2018 |

OTHER PUBLICATIONS

Extended European Search Report, EP Patent Application No. 18748530.5, dated Jan. 10, 2020.
Lucio, Carlos, et al., "Voluntary Cough Detection by Internal Sound Analysis," 2014 $7^{th}$ International Conference on Biomedical Engineering and Informatics, IEEE, Oct. 14, 2014, pp. 405-409.
Barry, Samantha J., et al., "The automatic recognition and counting of cough," Cough, Biomed Central, London, GB, vol. 2, No. 1, Sep. 28, 2006, pp. 1-9.
International Search Report issued in PCT/AU2020/051382 dated Apr. 12, 2021.
International Search Report in PCT/AU2020/051383, dated Apr. 14, 2021.

* cited by examiner

METHODS AND APPARATUS FOR COUGH DETECTION IN BACKGROUND NOISE ENVIRONMENTS

TECHNICAL FIELD

The present invention concerns methods and apparatus for processing sound from a subject, such as a patient, to detect cough sounds.

BACKGROUND ART

Any references to methods, apparatus or documents of the prior art are not to be taken as constituting any evidence or admission that they formed, or form part of the common general knowledge.

As is well known in the prior art, coughing is presented by a sudden air expulsion from the airways which is characterised by a well understood sound. According to Morice, A., Fontana, G., Belvisi, M., Birring, S., Chung, K., et al., "ERS guidelines on the assessment of cough", European Respiratory Journal, vol. 29, pp. 1256-1276, 2007, the audible cough sound of a one cough effort consist two or three phases as follows:
 1. Explosive phase—the 1 st cough sound
 2. Intermediate phase—steady airflow
 3. Voiced phase—aka the 2nd cough sound. This phase is not always present.

These three phases are identified for a typical cough sound in FIG. 1 which is a time domain amplitude plot of a cough sound recording.

According to Korpas J, Sadlonova J, Vrabec M: *Analysis of the cough sound: an overview*. Pulm Pharmacol. 1996, 9 (5-6): 261-10.1006/pulp.1996.0034.], the 3 phases are due to three different physical areas of the respiratory tract:
 1. Tracheal bifurcation—The Exposive phase reflects a pathological situation in the airways peripheral to the level of the tracheal bifurcation.
 2. Trachea—The intermediate phase reflects processes in the trachea.
 3. Laryngeal area—The voiced phase provides information about the laryngeal area.

In recent years it has become known to use automated approaches to processing sounds from human subjects to detect cough sounds.

For example, in US patent publication number US 2015/0073306 by Abeyratne at al., the disclosure of which is hereby incorporated by reference, there is described an apparatus that is specially configured to process sound from a patient and to identify passages of that sound as corresponding to a cough.

In general, there are two applications for a cough detection method, as follows:
 1. Cough counting—detecting coughs from a patient to make a count of the number of coughs detected in a given period; and
 2. Cough diagnosis—processing the detected cough sound to produce a disease diagnosis to subsequently assist in the provision of an appropriate therapy.

For cough counting it is only important to identify when a cough occurs, it is not necessary to be able to accurately define the start and end of a cough. However, for cough diagnosis it is important to be able to make the entire cough audio signal available for the automated cough diagnosis method, so it is very important to accurately define the start and end of a cough.

A reason why automated cough detection methods, such as those described in the previously mentioned US patent publication, are desirable is that the methods can be readily used in areas where low cost delivery of diagnostic services is needed. However, such areas often present difficulties to accurate diagnosis including high levels of street noise and other background sounds that cannot be readily avoided. For example, a medical professional in a crowded clinic in a lower socio-economic neighborhood on a busy road may have no option to sample the patient's sounds in a quieter environment.

Although the methods described in the previously mentioned US patent publication work well, the present Inventors have found that in particularly challenging circumstances the cough detection that is provided may not always be suitable for subsequent cough diagnosis. For example, challenging circumstances may include the cough sounds occurring in noisy backgrounds or the cough sounds being uttered in close succession, as my occur where the subject is a child.

It is an object of the present invention to provide an improved method and apparatus for detecting coughs present in patient sounds that are subject to background noise.

SUMMARY OF THE INVENTION

According to a first aspect of the present invention there is provided a method for detecting cough sounds from a sound wave including the steps of:
 acquiring the sound wave in electronic format;
 applying features extracted from the sound wave to at least two electronic pattern classifiers including a first classifier trained to detect an explosive phase of a cough sound and a second classifier trained to detect one or more post-explosive phases of the cough sound.

In a preferred embodiment of the present invention the method includes a step of applying the features extracted from the sound wave to the second classifier only after the first classifier has classified features of the sound wave as an explosive phase of a cough sound.

In a preferred embodiment of the method the first classifier is arranged according to a training that is positive in respect of the explosive phase and negative in respect of portions of the cough sound subsequent to the explosive phase.

Preferably the method includes providing a gap between the end of the explosive phase and commencement of said cough sound subsequent to the explosive phase.

In a preferred embodiment of the method the second classifier is arranged according to training that is negative in respect of the explosive phase and positive in respect of portions of the cough sound subsequent to the explosive phase.

Preferably the second classifier is arranged according to the previously mentioned training wherein a gap is provided between the end of the explosive phase and commencement of said cough sound subsequent to the explosive phase.

In a preferred embodiment of the present invention the features include features corresponding to mel-frequency cepstral coefficients of the sound wave.

Preferably the features further include a feature corresponding to log-energy of the sound wave.

Preferably the first and second classifiers comprise time delay neural nets.

According to a further aspect of the present invention there is provided an apparatus for detecting cough sounds of a sound wave including: a digitizing assembly for digitizing output from a transducer for transducing the sound wave;
a feature extraction assembly in communication with the digitizing assembly for extracting a plurality of features from consecutive segments of the sound wave;
a first classifier responsive to the feature extraction assembly trained to recognize an explosive phase of a cough sound;
a second classifier responsive to the feature extraction assembly trained to recognize one or more post-explosive phases of the cough sound; and
a post-classifier cough identification processor arranged to identify the cough sounds based on outputs from the first classifier and the second classifier.

Preferably the post-classifier cough identification processor is arranged to respond to the output from the second classifier subsequent to the output from the first classifier indicating detection of an explosive phase of the cough sound.

In a preferred embodiment of the invention the first classifier and the second classifier comprise first and second neural nets wherein the first neural net is weighted in accordance with positive training to detect the explosive phase and wherein the second neural net is weighted in accordance with positive training to detect the one or more post-explosive phases.

It is preferred that the first neural net is further weighted in accordance with positive training in respect of the explosive phase and negative training in respect of the post-explosive phases.

It is also preferred that the second neural net is further weighted in accordance with negative training in respect of the explosive phase and positive training in respect of the post-explosive phases.

In a preferred embodiment of the invention the feature extraction assembly is arranged to extract mel-frequency cepstral coefficients (MFCCs) from the sound wave.

Preferably the feature extraction assembly is arranged to extract MFCCs including a zeroth order MFCC.

It is preferable that the feature extraction assembly is arranged to extract a log-energy feature of the sound wave.

In a preferred embodiment of the invention the apparatus includes first and second comparators for comparing outputs from the first and second classifiers to threshold values for gauging respective detection probability levels of the explosive phase and the post explosive phase.

In a preferred embodiment of the invention the cough identification processor is responsive to the comparators for identifying the cough sounds.

Preferably the cough sound identifier includes an RMS power estimator for estimating the RMS power of segments of the sound wave wherein the cough identification processor is arranged to identify the cough sounds taking into account output from the RMS power estimator.

It is preferred that the apparatus includes a cough flagger assembly that is responsive to the post-cough identification processor, wherein the cough flagger assembly is arranged to record portions of the sound wave identified to contain cough sounds.

The first and second neural nets preferably comprise time delay neural nets which process a sequence of time delayed feature vectors emanating from the feature extraction assembly.

The apparatus may be implemented by means of a portable computational device specially programmed according to the previously described method.

According to another aspect of the present invention there is provided a method for detecting cough sounds from a sound wave including the steps of:
applying features extracted from the sound wave to an electronic pattern classifier, the pattern classifier being configured to detect an explosive phase of a cough; one or more post-explosive phases of the cough sound; and the presence of a non-cough event; and
deeming a cough to be detected taking into account signals from the electronic pattern classifier corresponding to detection of the explosive phase, the one or more post-explosive phases and the presence of a non-cough event.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DETAILED DESCRIPTION OF PREFERRED EMBODIMENTS

The Inventors have found that presently available methods for cough detection may fail to distinguish coughs that are close together (e.g. a 'train' of coughs one-after-each-other) which is a fairly common occurrence in recordings of children coughing.

Figure 2:
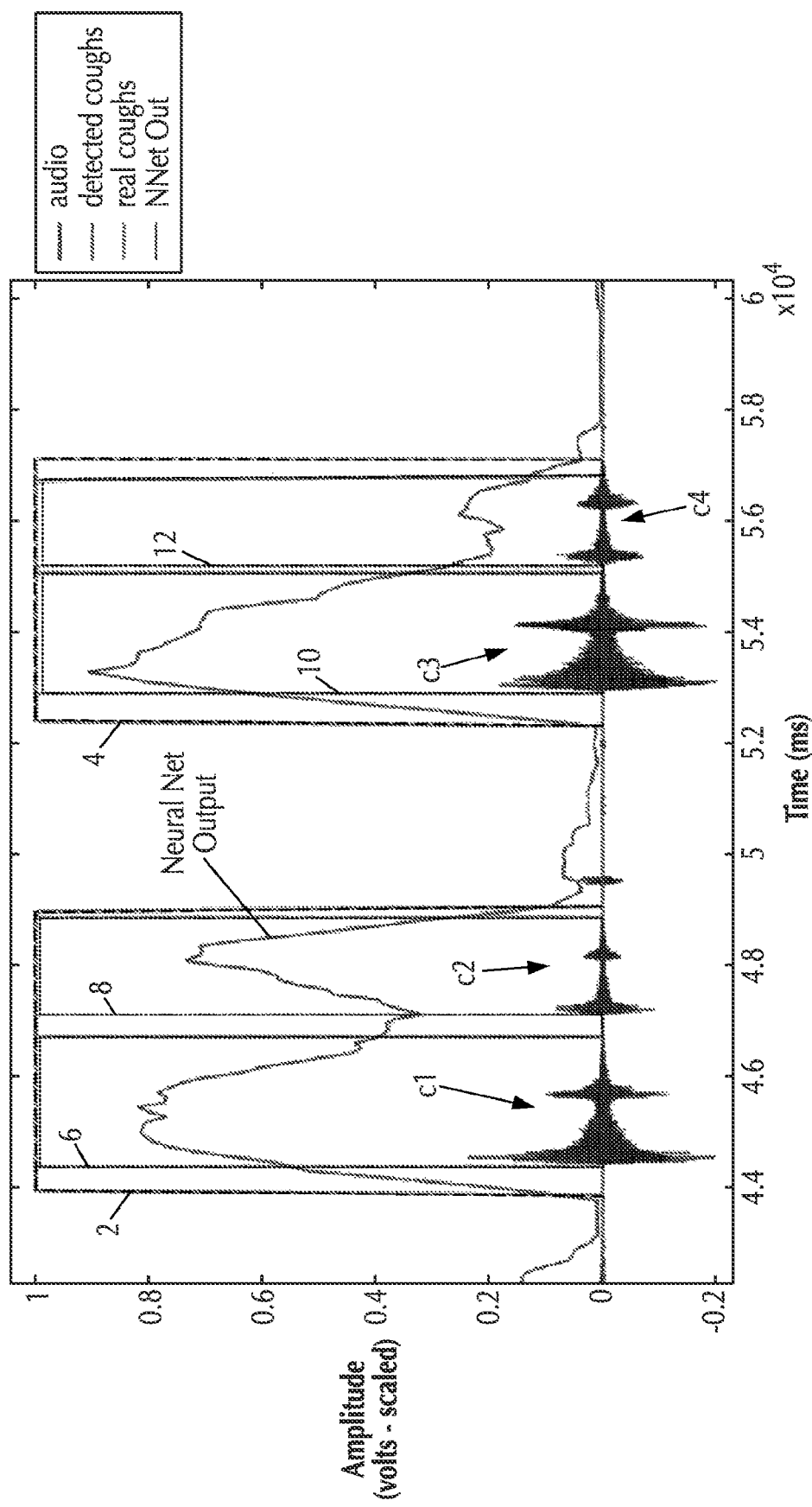
FIG. 2 is a plot of two consecutive cough sound waveforms with classification of the coughs according to prior art method superimposed thereon.
Figure 3:
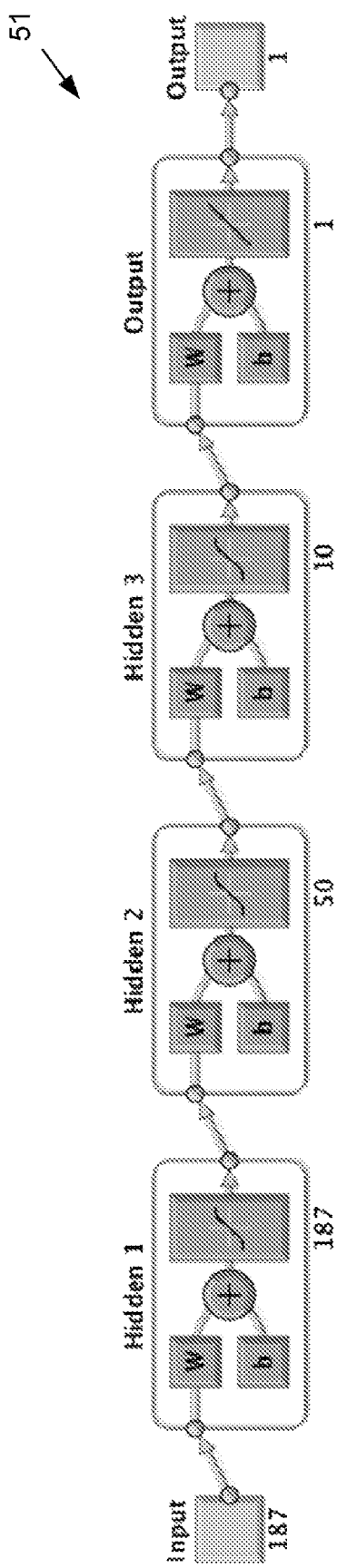
FIG. 3 is a block diagram of a neural net classifier of the prior art used in generating the classification illustrated in FIG. 2.

FIG. 2 is a plot of a sequence of four coughs c1, . . . , c4 with the output 2 of a neural net implemented cough detection apparatus of the prior art superimposed thereon. The neural net-arrangement 51 that was used is described in US 2015/0073306 and is illustrated in FIG. 3. With reference to the plot of FIG. 2, it will be seen that in this example the prior art method fails to correctly detect sets of coughs in close proximity, i.e. c1, c2 and c3, c4 into four discrete coughs. Instead c1 and c2 are deemed to be a single cough as indicated by line 2 and c3 and c4 are also deemed to be a single cough as indicated by line 4. The true identification of the coughs, as might be achieved by a human listener is indicated by lines 6, 8, 10 and 12.

Before conceiving the present invention, a preferred embodiment of which will be described later, the present Inventors tried several different approaches to improve on the prior art. For example, a first attempt that is referred to herein as the "LW1" method, was designed to reduce the number of the hand-crafted features, reduce the complexity of the neural network and train the neural network only on processing frames of the audio signal which had a root mean square (RMS) power value that exceeded the average RMS of the whole cough event.

Figure 4:
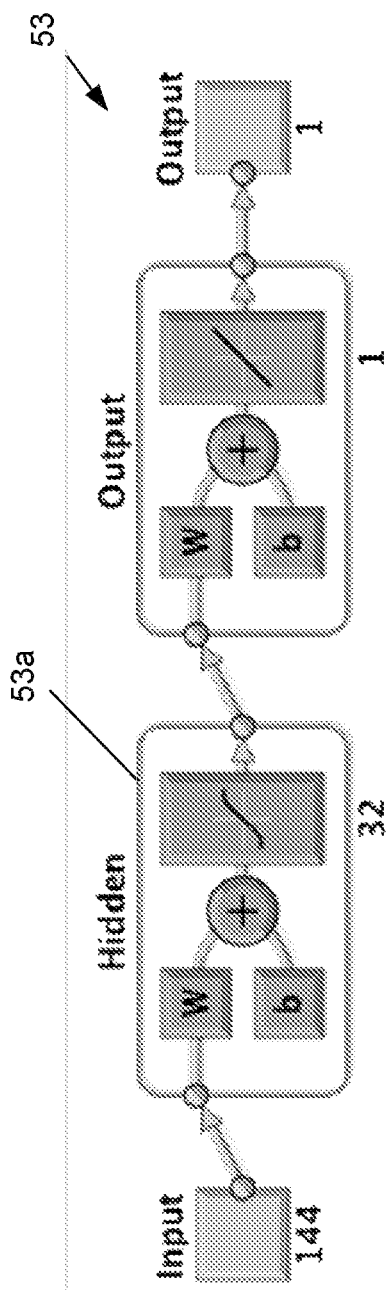
FIG. 4 is a block diagram of a neural net architecture of the LW1 algorithm that is discussed herein.

The reduced feature set that the Inventors used in this initial approach included mel-frequency cepstral coefficient (MFCC) features, zero-crossing rate and Shannon entropy. The size of the neural network (NN) 53 was reduced from three hidden layers with 187, 50 and 10 nodes respectively, to only one hidden layer 3a with 32 nodes as illustrated in FIG. 4. The NN 3 of FIG. 4 was then trained with frames of the training sound sample having an RMS power value above the mean RMS of the cough. Low energy frames were ignored in the training process. In addition, a number of speaking, clapping, sounds of machines, and other non-cough typical background sounds were used as negative examples.

As may be seen from Table 1, LW1 was found to provide significantly increased accuracy over the prior art method. Especially for coughs that were close together, coughs in noisier environments and coughs recorded using different microphones. In general it was a significantly more robust solution that that described in the previously mentioned US patent publication.

TABLE 1 performance of the prior art algorithm and LW1 on very challenging cough, i.e. high background noise level, recordings and/or many coughs occurring close together.

|  | Recall (%) | Precision (%) | F1-Score |
|---|---|---|---|
| Prior Art Method | 50 | 50 | 0.0.50 |
| LW1 | 53 | 88 | 0.66 |

Figure 5:
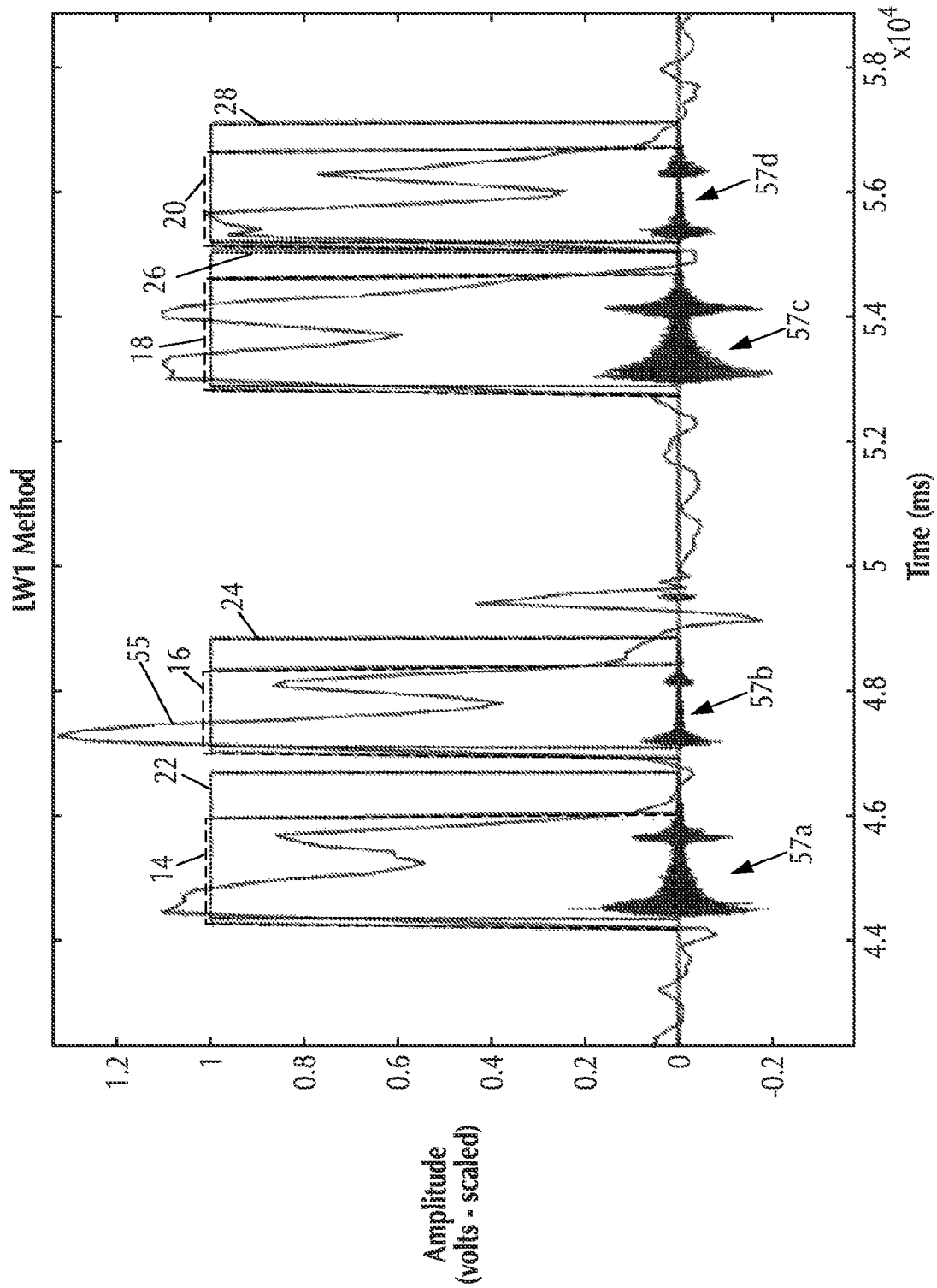
FIG. 5 is a plot of two sets of two cough sounds close together with classification of the cough sounds according to the LW1 method superimposed thereon.

FIG. 5 presents a plot of the output 55 of the NN 53 of FIG. 4 trained to implement the LW1 method with the output superimposed on four consecutive cough sounds 57a-57d. It will be observed that the LW1 method correctly detects two sets of two coughs close together as indicated by lines 14, 16 and 18, 20. However, it will also be observed that the detected coughs are cut short compared to hand-marked true coughs as indicated by lines 22, 24, 26, and 28. The Inventors considered LW1 to be a highly accurate cough detector method and very useful for cough counting applications, however it was failing to give an accurate measure of when the cough ended which is required for automated cough diagnosis.

Consequently, the Inventors resolved to try another, second attempt, which is herein called the "LW1.5" method.

In the LW1.5 method a neural network was trained only on the first cough sound, i.e. the explosive phase of the cough. The training was done such that from the onset of a cough four processing frames (app. 100 ms) were trained as a positive target and the rest of the hand marked cough was trained as a negative target. Another change was to reduce further the number of the hand-crafted features to include only the MFCCs and the log-energy of the signal.

As with LW1, energy based heuristics were used in the LW1.5 method to extend the cough detection. In this attempt the Inventors extended the cough based on estimated minimum background noise level. The background noise level was estimated by taking 1024 lowest energy frames in the recording to the current point and taking the mean RMS. The cough was terminated when the RMS of a processing frame dropped below 1.5 times the estimated background level.

As can be seen from Table 2, the recall percentage that was achieved with LW1.5 is much better than was the case for LW1. However, the precision dropped 10% which the Inventors felt was unsatisfactory.

TABLE 2 performance of the LW1 method and LW1.5 on very challenging, i.e. high background noise, cough data

|  | Recall (%) | Precision (%) | F1-Score |
|---|---|---|---|
| LW1 | 53 | 88 | 0.66 |
| LW1.5 | 61 | 81 | 0.70 |

It will therefore be realized that at this stage two different approaches had been conceived and tested. However in the Inventors' view whilst both methods were improvements in different ways, neither the LW1 nor the LW1.5 method were suitable for detecting coughs to a standard that the detected coughs might subsequently be processed for disease diagnosis.

After much thought a breakthrough occurred in which the Inventors, contrary to their previous attempts, decided to try more than one neural network for cough detection.

The Inventors decided, in a preferred embodiment of the present invention, sometimes referred to herein as "LW2", to use a second neural network in an attempt to classify the second and third phases of the cough event. It is important to note that these second and third phases (in particular the third, voiced phase) are not unique to cough events. For example, voiced events occur often during speech. If the second neural network was used by itself, there would be a significant number of false positives due to speech and other human noises. Consequently, the Inventors were unsure whether such an approach would be successful.

As an overview, in the preferred embodiment of the invention the Inventors processed the output from two trained neural networks to detect cough sounds. The first neural network was trained (as in method LW1.5) to classify the first, explosive phase of the cough sound and the second neural network was trained to classify the second and third phases of the cough sound. To avoid the problem of the second network producing false positives during speech, the method preferably includes a temporal combination of the two NNs so that activation of the second NN follows the first NN.

Steps to Extract a Single Cough Effort

Figure 5A:
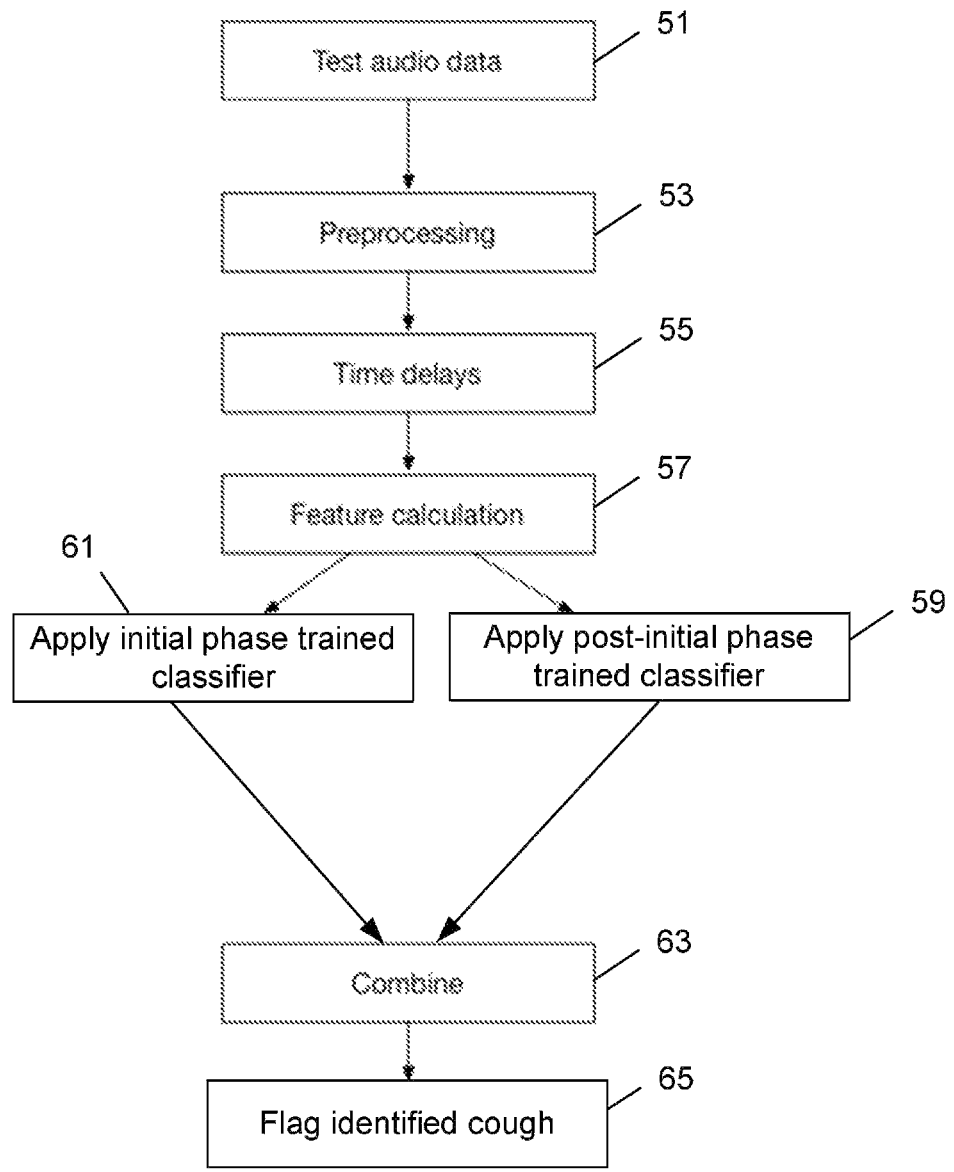
FIG. 5A is a flowchart of a method for detecting cough sounds according to a preferred embodiment of the present invention.

FIG. 5A is a flowchart of a method for cough detection according to a preferred embodiment of the present invention. Initially at box 51 test audio data, which potentially contains cough sounds, is acquired, for example by recording a patient with a microphone of a digital recorder. At box 53 the test audio data is preprocessed by high and low pass filtering and analog to digital conversion. At box 55 the digitized sound signal is segmented into frames and time delays are applied so that the signal can be applied to time delay neural net classifiers. At box 57 each frame of the digitized signal is analysed to determine the presence of certain features, in the preferred embodiment of the invention these features include mel-frequency cepstral coefficients (MFCCs) and a signal log-energy feature.

The detected features are formed into a series of feature vectors. In box 61 a classifier in the form of a time delay neural network (TDNN) that has been pretrained to identify the first explosive phase of a cough examines a series of the frames to determine whether or not that explosive phase is present. At box 59 a second time delay neural network that has been pre-trained to identify the second and third phases of a cough examines the frames to determine if the second and third phases are present.

In box 63 the outputs from the TDNN classifiers are smoothed and compared to predetermined threshold values to determine whether or not the frames correspond to a cough signal. At box 65, if the frames were detected to indicate the presence of a cough then the cough is flagged, for example by writing a record of the particular portions of the audio signal that convey the detected cough.

Figure 6:
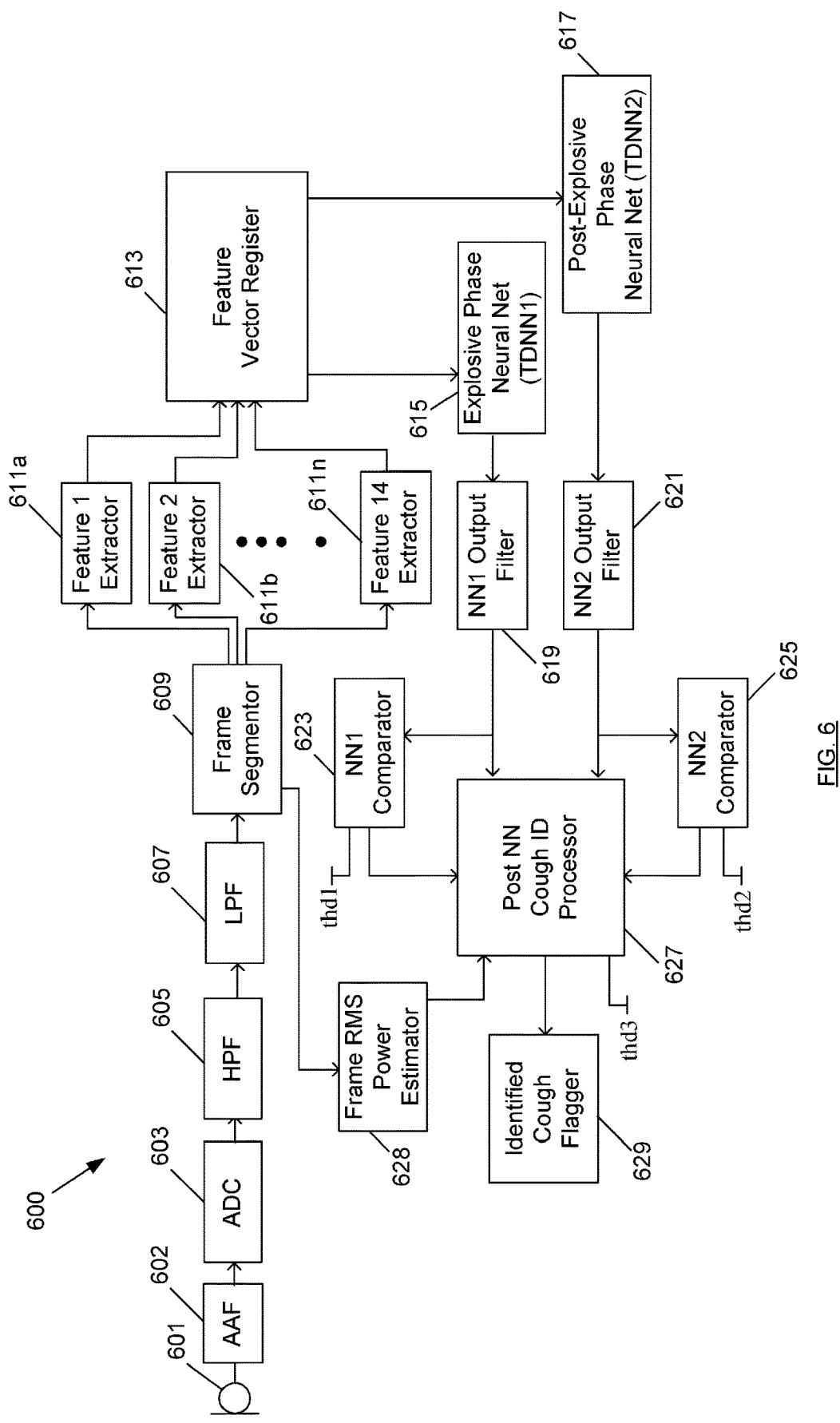
FIG. 6 is a block diagram of an apparatus according to an embodiment of the present invention for implementing the method of FIG. 5A.

Referring now to FIG. 6, there is depicted a block diagram of a cough detector 600 for identifying cough sounds according to a first embodiment of the present invention which implements the method of the flowchart of FIG. 5A.

Preprocessing

Audio signal from the subject is transduced by microphone 601 and subjected to anti-aliasing filtering by filter 602. The filtered analog signal from the AAF filter 602 is passed to analog-to-digital converter 607. The digitized signal from ADC 603 is high and low pass filtered by filters 605 and 607 as a first step in the digital signal processing pipeline. In the presently described embodiment of the invention the cut-off frequency of the high pass filter 605 is 50 Hz and the cut-off frequency of the low pass filter 607 is 16 kHz.

Feature Extraction

The digitized and filtered audio signal from the LPF 607 is segmented into 1024 samples of non-overlapping frames by frame segmentor 609. Each frame, represents 23.2 ms of audio duration. Fourteen feature values are extracted for each frame by feature extractor assemblies 611a, 611n. In the presently described preferred embodiment of the invention the features that are extracted comprise thirteen Mel-Frequency Cepstral Coefficients (MFCC) including the zeroth coefficient and also a feature corresponding to the log-energy of each frame. The output from the feature extractors 611a, . . . , 611n are passed to a sequential feature vector register 613. Each feature vector stored in the register 613 has values for the corresponding fourteen extracted features.

The feature vectors from feature vector register 613 are applied to each of two specially trained first and second time delay neural nets 615 and 617. The TDNNs 615 and 617 have been respectively trained, in a manner that will be explained. The trained TDNN1 615 detects the explosive phases of the cough sound whereas TDNN2 is trained to detect the remainder of the cough, that is the post-explosive phases.

The outputs from the first and second TDNNs 615 and 617 are coupled to respective NN1 and NN2 smoothing filters 619 and 621. The NN1 smoothing filter 619 output is a 3-tap averaging filter. The NN2 smoothing filter 621 is a 5-tap averaging filter.

The output from the NN1 Output filter 619 is applied to a comparator 623 which compares the signal from the NN1 Output Filter 619 with a threshold level thd1. The output from the NN1 Comparator 623 indicates if the output from the NN1 Output filter is above thd1 or if it is below.

Similarly, the output from the NN2 Comparator 625 indicates if the output from the NN2 Output filter is above thd2 or if it is below.

The Post NN Cough ID Processor 627 comprises a logic assembly that is configured to decide whether or not the outputs from the NN1 and NN2 Output Filters 619 and 621 and the outputs from the NN1 and NN2 comparators indicate the presence of a cough sound in the sound signal being processed. The Post NN Cough ID Processor 627 may be implemented as a discrete logic board or alternatively it may comprise a programmed controller such as a field programmable gate array (FPGA) or a suitably programmed microprocessor.

The Post NN Cough ID processor 627 is configured to operate according to the following rules.

1. Potential cough identification commences only when NN1 is higher than the fixed threshold (thd1). A start of a cough will always require onset of NN1.
2. A potential cough identification continues if:
    I. NN1 is above threshold (thd1);
    II. NN1 is below threshold (thd1) and NN2 is above threshold (thd2);
    II. The output from the Frame RMS Power Estimator 628 indicates that the RMS power of a frame is higher than 10 times the estimated background noise RMS level. The Frame RMS Power Estimator is arranged to estimate background noise level by averaging 1024 lowest RMS frames during the recording thus far. The RMS based continuation is incorporated because sometimes there is a gap between NN1 and NN2. The RMS based bridging is done only when no NN2 frames are yet detected.

3. Cough is terminated when:
   I. The output from the NN1 Output filter 619 is crossing the output from the NN2 Output filter 621 in an upward direction
   II. The output from the NN1 comparator 623 indicates that the output from the NN1 Output Filter 619 is below thd1; and the output from the NN2 Comparator 625 indicates that the output from the NN2 Output Filter 621 is below thd2 and the output from the Frame RMS Power Estimator 628 indicates that the RMS power of the frame is less than ten times the estimated background noise level.
   III. The output of the NN1 Output Filter 619 for the current frame (t) is greater than thd1, the output of the NN1 Output Filter 619 for the previous frame t−1) is less than thd1 and In the current (potential) cough event detected NN2 frame(s) have been detected that have resulted in the output from NN2 comparator going high (i.e. the output from NN2 Output filter 621 exceeding thd2).
4. A found cough is discarded if:
   I. The cough's duration is less than a minimum length of a cough (150 ms)
   II. The cough's duration is more than a maximum length of a cough (750 ms)
   III. The combined RMS power outputs of the NN1 Output Filter 619 and the NN2 Output Filter 621 of the cough is below a predetermined threshold value thd3, which is determined during the training process.
   IV. Less than 3 frames of the output of the NN1 Comparator 623 indicate an above threshold level thd1 in the cough
   V. Less than 2 frames of the output of the NN2 Comparator 625 are indicated as being above threshold thd2 in the cough
5. The beginning of the detected cough is trimmed to a sudden onset of energy on short processing frames (128 samples). If an onset is detected, the cough start time is adjusted accordingly. If no jump in the energy level is detected, then the start time is left at the processing frame boundary.

Figure 6A:
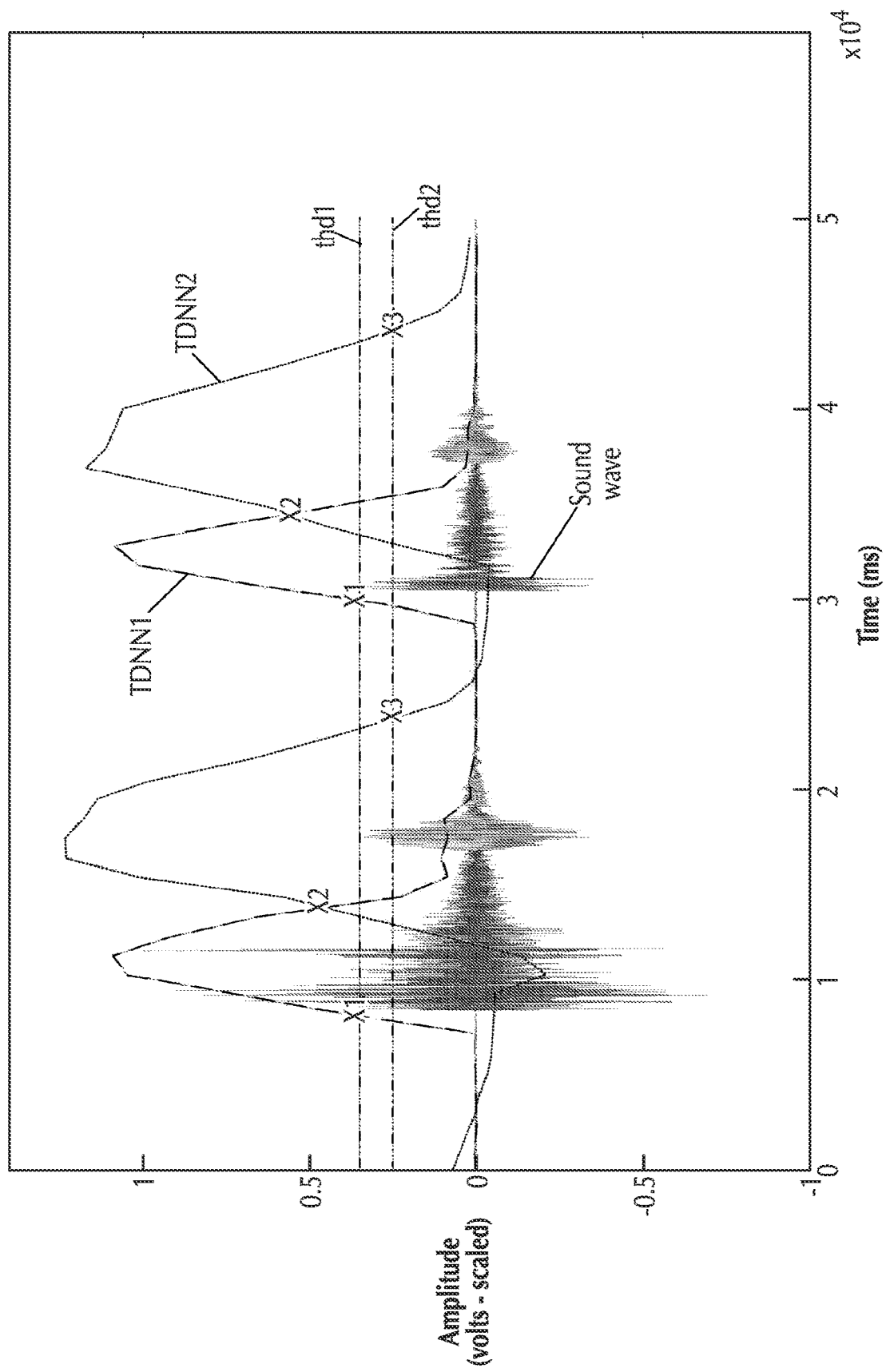
FIG. 6A is a block diagram of a cough sound with outputs from classifiers of the preferred embodiment superimposed thereon for explaining various threshold values used in the performance of the preferred embodiment of the invention.

Referring now to FIG. 6A, the derivation of the thd3 value that is mentioned in 4.III above will be explained.

The RMS of TDNN1 output is calculated from X1 to X2=rms_nn1.

The RMS of TDNN2 output is calculated from X2 to X3.=rms_nn2

X1=TDNN1>thd1

X2=TDNN2>thd2 and TDNN2>TDNN1

X3=TDNN2<=thd2

The total RMS of the cough probability is rms_nn1+rms_nn2. This describes the intensity of the probability above both networks above the thd1 and thd2. This total RMS is compared to thd3 to determine if the potential cough has high enough RMS regarding the outputs of the two neural networks.

The thd3 value is determined in the training phase such that the false positives and true positives are optimized by searching a range of thresholds.

It should be noted that sometimes the X2 is split into two. In this case both nn1 and nn2 are below the thresholds 1 and 2 in the intermediate phase so that:

rms_nn1=rms of nn1 from (TDNN1>thd1) to (TDNN1<=thd1)

rms_nn2=rms of nn2 from (TDNN2>thd2) to (TDNN2<=thd2)

That is, the probability RMS is not calculated if both networks are under the thresholds.

The cough detection apparatus 600 includes an Identified Cough Flagger assembly 629 which receives an output from the Post NN Cough ID Processor 627 that indicates the start and the end of a detected cough sound. The Post NN Cough ID Processor 627 responds to signals from the Post NN Cough ID Processor by flagging the identified coughs. Flagging the identified coughs may involve writing a data record containing an ID number for the cough along with its starting time in the sound wave and its end time. The Identified Cough Flagger 629 may include a visual display that displays the cough ID and associated start and end times.

Performance of the Preferred Embodiment

A prospective study of the cough identification algorithms was undertaken where cough recordings of children were made by experienced healthcare professionals in India. These recordings were made in environments which contained significant background noise, including talking, car horns, music and machine-generated noise. The NN were trained on other reference data and were tested on 52 recordings.

TABLE 2 performance of the prior art method, LW1, LW1.5 and LW2 on very challenging cough recordings. None of the algorithms were not trained on this data.

|  | Recall (%) | Precision (%) | F1-Score |
|---|---|---|---|
| Prior Art Method | 35 | 45 | 0.39 |
| LW1 | 46 | 91 | 0.61 |
| LW1.5 | 61 | 81 | 0.70 |
| LW2 | 80 | 90 | 0.85 |

Figure 7:
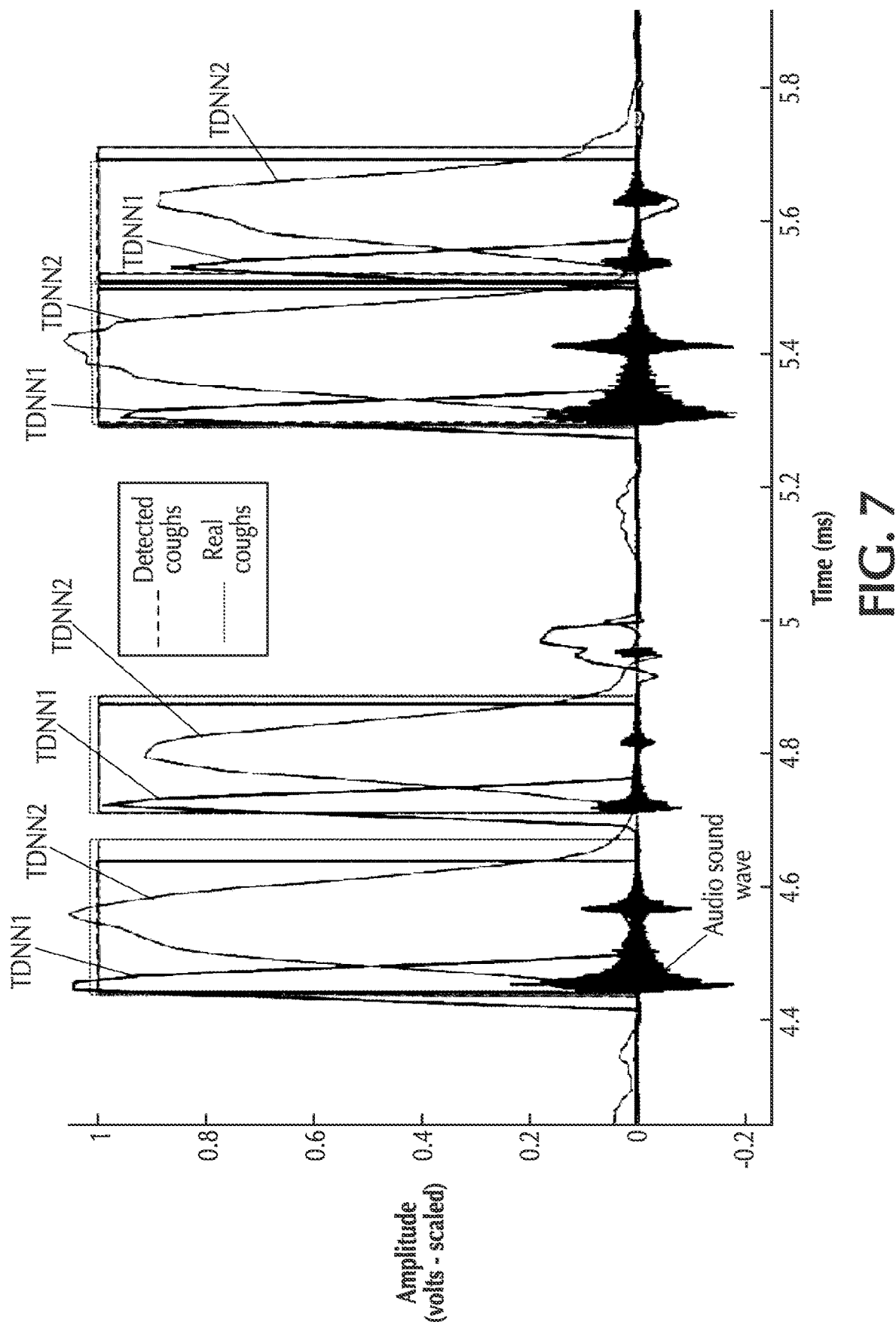
FIG. 7 is a plot of two sets of two cough sounds close together with classification of the cough sounds according to the method of the flowchart of FIG. 5A superimposed thereon.

FIG. 7 graphically illustrates cough detection with LW2. As can be seen from FIG. 7, the detected coughs line closely matches the actual coughs. LW2 captures the duration of the coughs better than LW1.

Training NN1 and NN2

As previously mentioned, the preferred embodiment of the invention requires that two time delay neural networks are trained. TDNN1 615 is trained to detect the initial cough sounds that is the explosive phase of each cough. The second network TDNN2 617 is trained to detect the rest of the cough, including the intermediate phase and the voiced cough sound, if present.

It is a common knowledge that the first cough sound has very distinctive characteristics and it is more consistent between the subjects than the other parts of the cough sound. For example, previously researchers have made the following comments:

"In our approach we leverage the fact that the first 150 ms of a cough sound corresponds only to the explosive phase of the cough reflex and is generally consistent across observers. We only model this explosive stage of the cough reflex so that our model can generalize across observers." Eric C. Larson, TienJui Lee, Sean Liu, Margaret Rosenfeld, and Shwetak N. Patel. 2011. *Accurate and privacy preserving cough sensing using a low-cost microphone.* In Proceedings of the 13th international conference on Ubiquitous computing (UbiComp '11). ACM, New York, NY, USA, 375-384. DOI=http://dx.doi.org/10.1145/2030112.2030163; and "Our approach relies on explosive phase detection, because of its acoustic and spectral distinctive characteristics, and its potential for accurate onset detection of cough sounds." Lucio C, Teixeira C, Henriques J, de Carvalho P, Paiva R P. *Voluntary cough detection by internal sound analysis.* In: Biomedical Engineering and Informatics (BMEI), 2014 7th International Conference on; 2014. p. 405-409.

In the preferred embodiment of the present invention the start of a potential cough is detected based only on the first neural network which is trained to find the explosive phases of the coughs. The second neural network is used to detect the rest of the cough event.

Figure 7A:
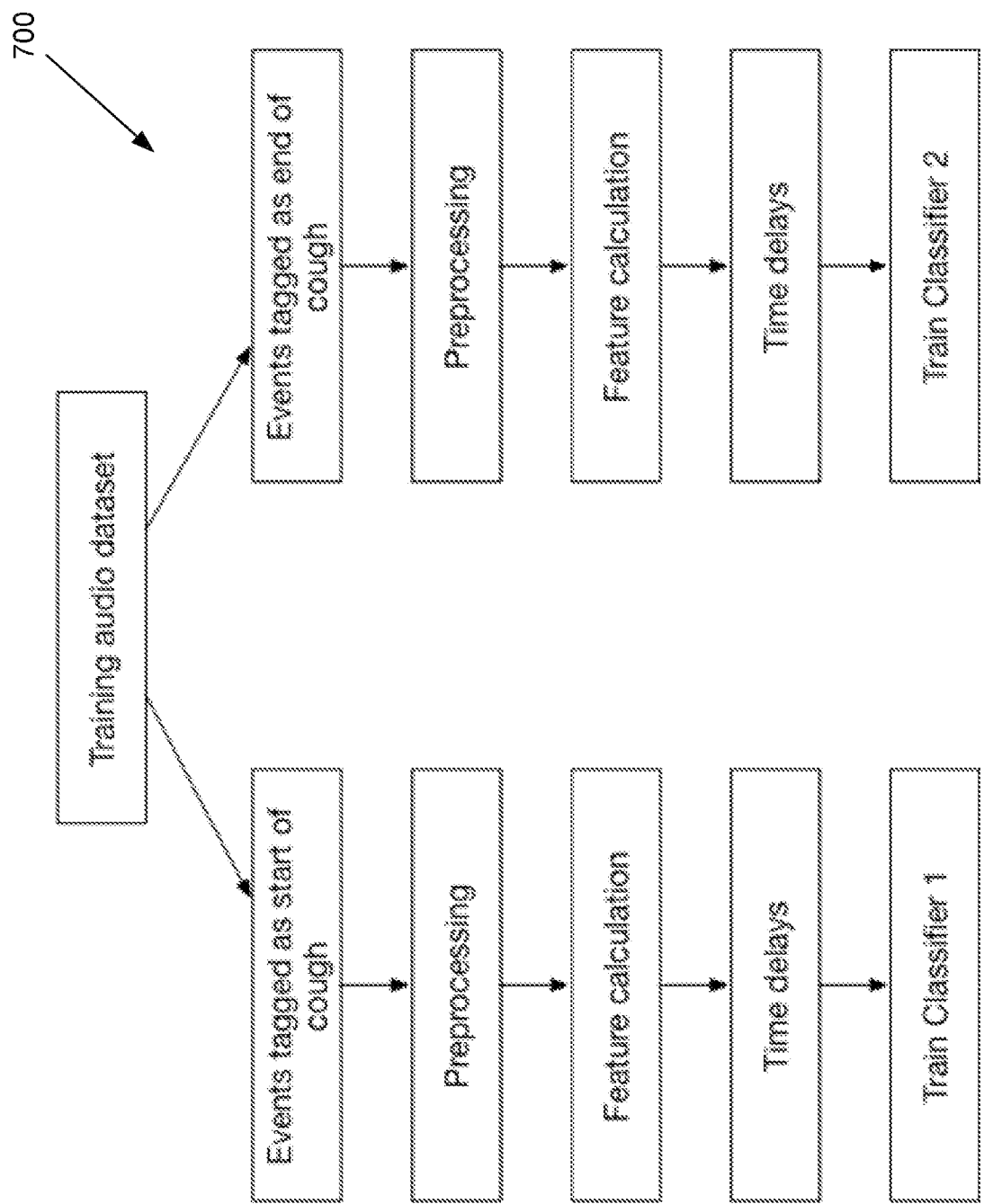
FIG. 7A is a flowchart of a method for training first and second classifiers according to a preferred embodiment of an aspect of the present invention.

FIG. 7A presents a high level block flowchart 700 of a method for training a first classifier, e.g. Explosive Phase Neural Net (TDNN1) 615 and a second classifier, e.g. Post-Explosive Phase Neural Net (TDNN2) 617.

Training the First Neural Network—Classify the Explosive Phase of the Cough

Figure 8:
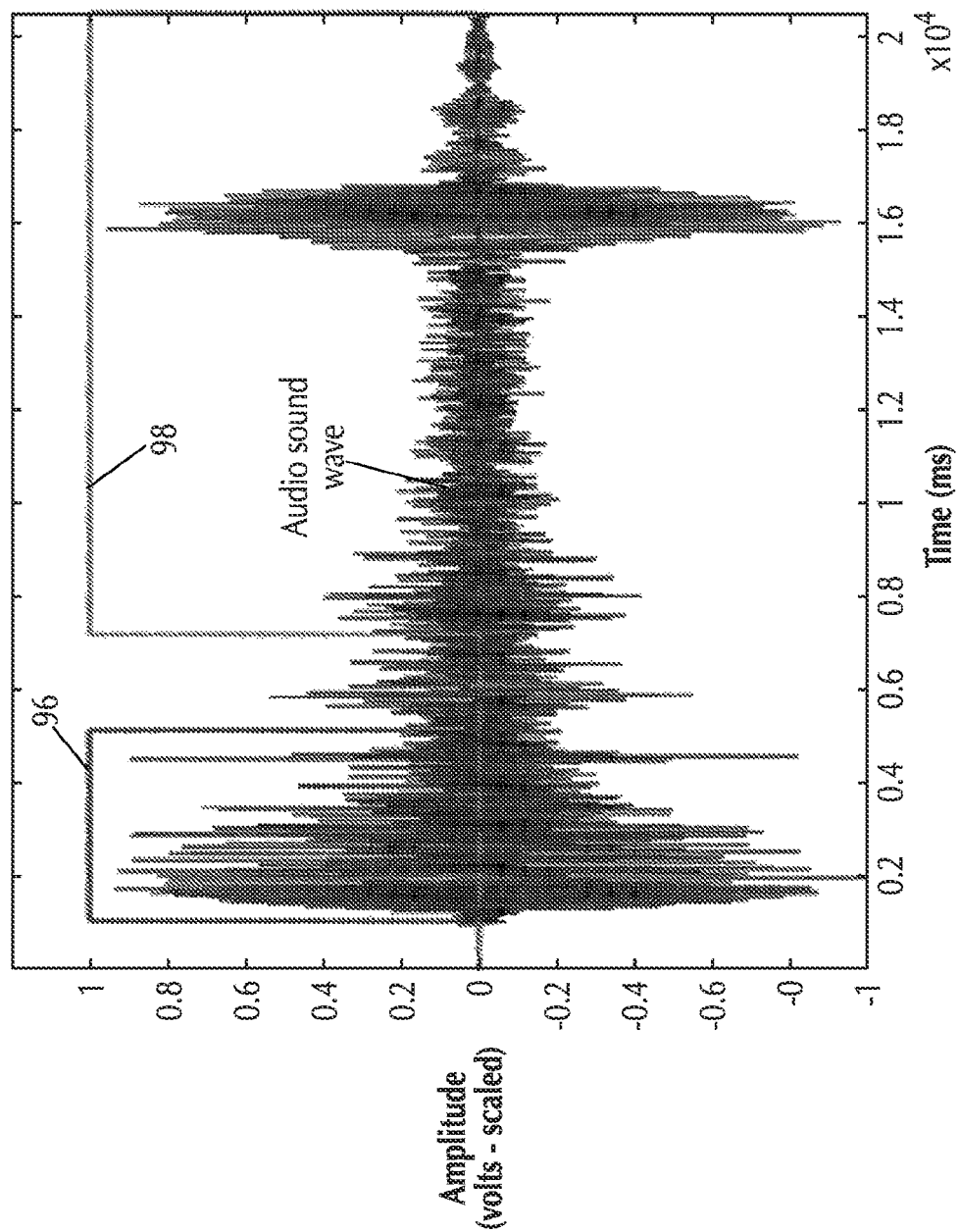
FIG. 8 is a plot of a cough sound waveform indicating portions of the waveform from which features are taken to to positively and negatively train the first classifier for detecting an initial explosive phase of the cough sound.

The first network is trained on four processing frames starting from the first frame of the hand marked cough which RMS (Root Mean Square) is higher than the average RMS of the whole cough sound. The rest of the hand marked cough is trained as a negative target. Two processing frames between the target and the negative target are not trained at all to reduce confusion. The negative example are trained as such. FIG. 8 illustrates the parts of the cough that are trained as positive (line 96) and negative (line 98) targets for the first neural network 615. In addition, examples of speech, crying, clapping and machine-generated noise are used as negative training examples.

Figure 9:
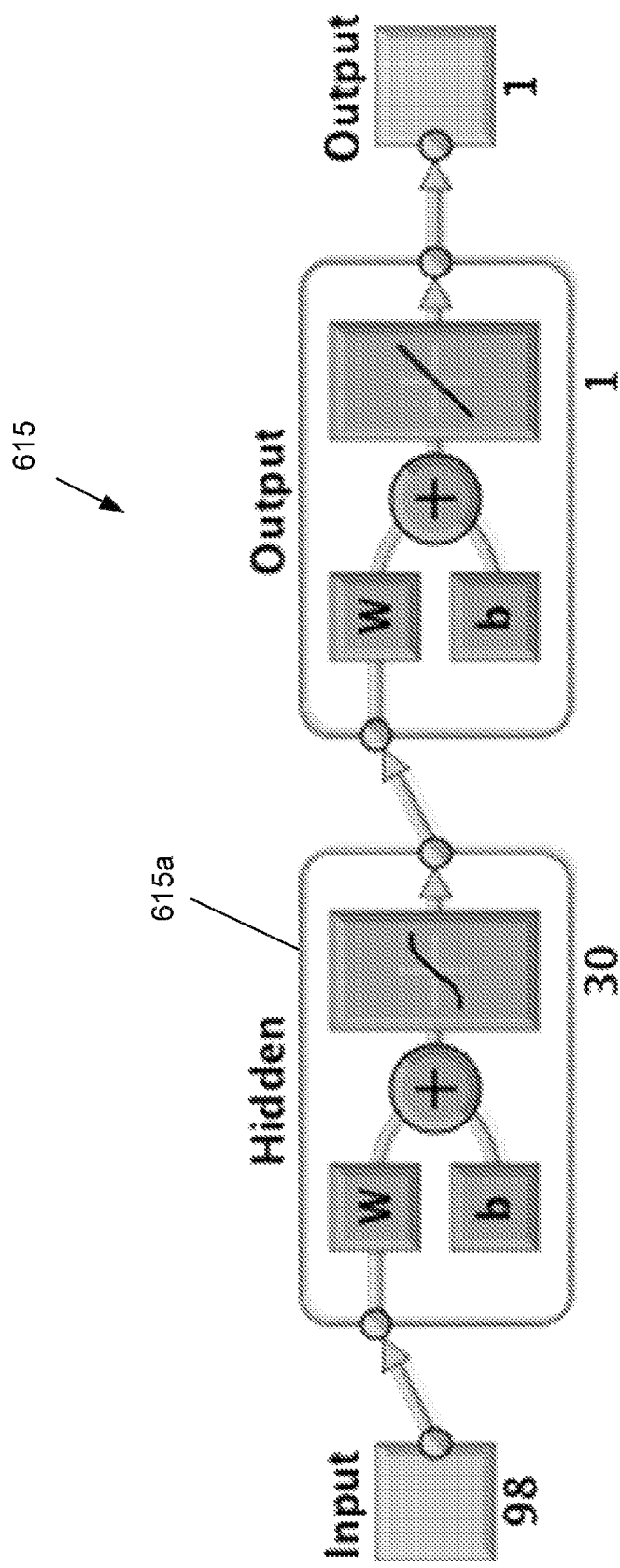
FIG. 9 is a block diagram of the structure of preferred classifiers used according to the present invention.

The input of the TDNN1 615 includes a feature vector derived from processing seven frames, where the target frame is the middle one. That is the input vector "sees" three neighbouring frames before and three frames after the target frame. Thus the size of the input vector for the TDNN is 7×14=98 values. FIG. 9 is a block diagram of an architecture for TDNN1 615. Whilst the architecture illustrated in FIG. 9 works well the Inventors have found that sixteen nodes rather than thirty in the hidden layer may work even slightly better. It will be realized that other configurations for TDNN1 and TDNN2 may also work.

Training the Second Neural Network—Classifying the End Phases of the Cough

Figure 10:
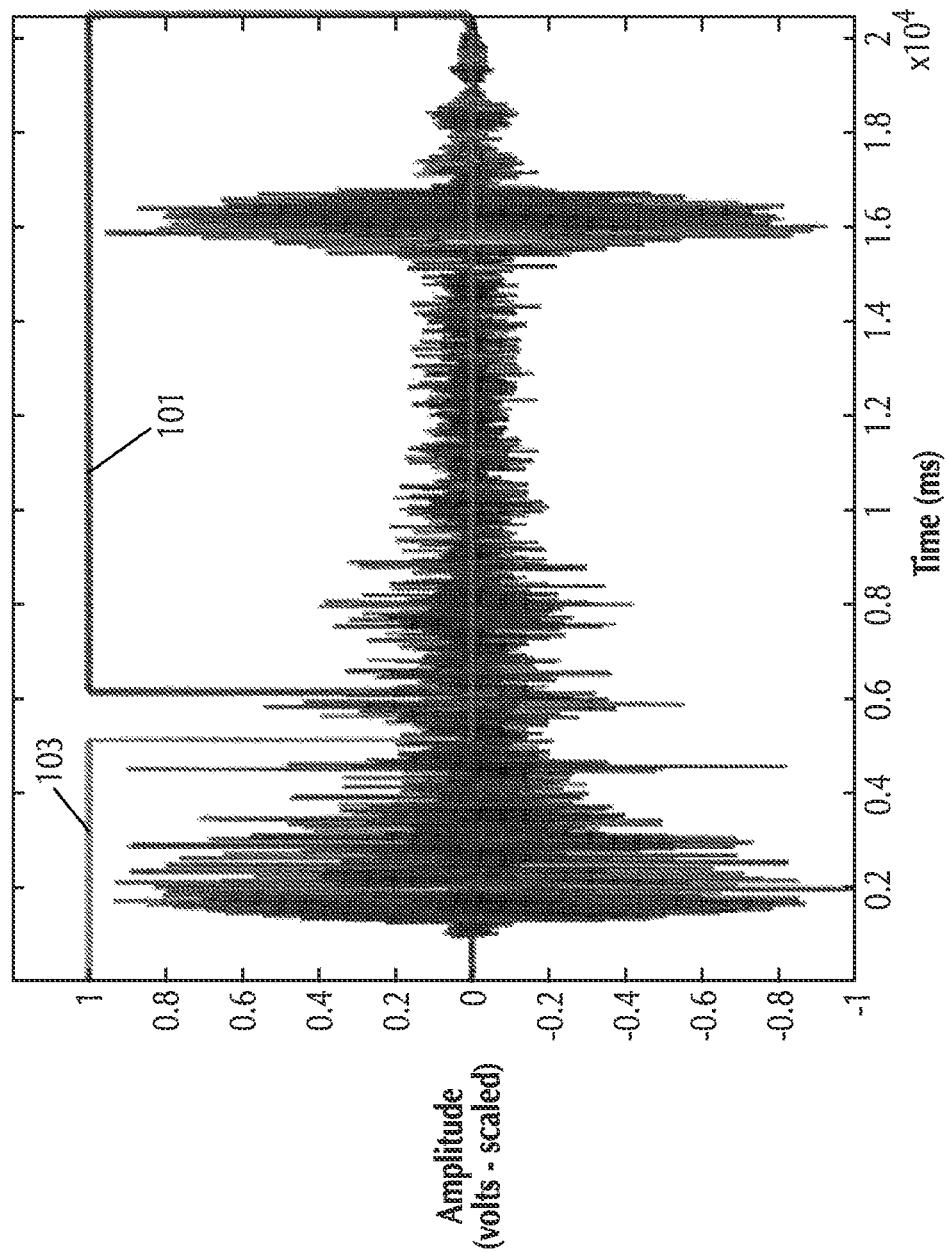
FIG. 10 is a plot of a cough sound waveform indicating portions of the waveform from which features are taken to positively and negatively train the second classifier for detecting post-explosive phases of the cough sound.

The second network TDNN2 617 is trained in an opposite manner to the first one. The very beginning of the cough and the first four frames from the onset are trained as negative targets. One frame is skipped in between and then all the rest frames of the cough are trained as positive target if their RMS is higher than 0.1 times the mean RMS of the whole cough signal. Very low energy frames which resample a lot the background noise are dropped. Again the negative examples are trained as such. FIG. 10 illustrates the parts of a cough that are trained as positive 101 and negative 103 targets for the second neural network.

Figure 11:
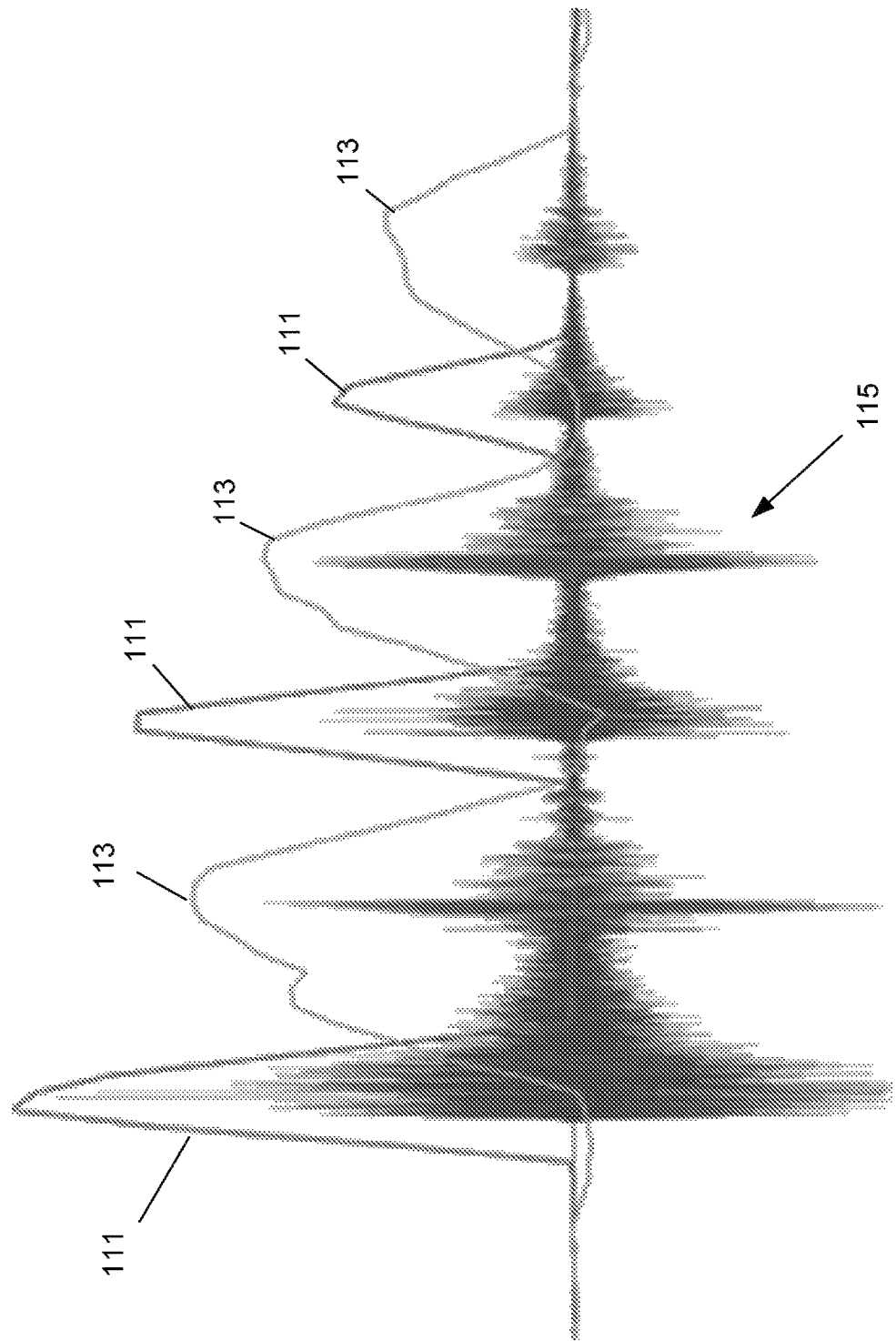
FIG. 11 is a plot of a sequence of cough sounds with output from the first and second classifiers superimposed thereon.

As previously discussed, cough detection is based on the output of the two trained neural networks of a continuous stream of features extracted from the audio signal and fed to the two networks. FIG. 11 shows the output 111 of the trained initial phase detecting neural network TDNN1 615, and the output 113 of the subsequent phases detecting neural network TDNN2 617, in response to a burst of three connected coughs 115.

Figure 12:
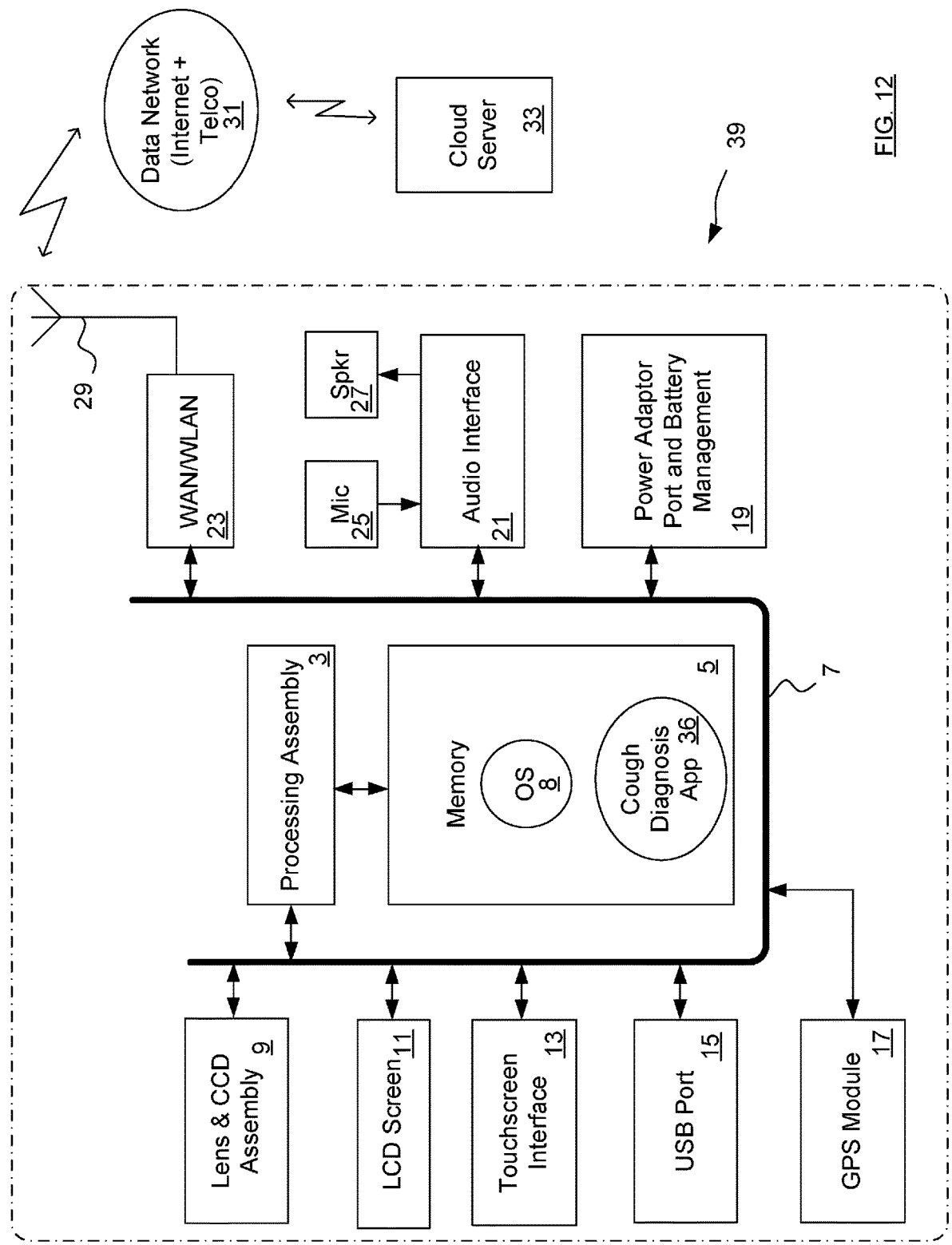
FIG. 12 is a block diagram of a cough detection apparatus comprising a specially programmed portable computational device in the form of a smartphone.

The cough detection method that is set out in the flowchart of FIG. 5A may be implemented by specially programming a portable computational device such as a smartphone. FIG. 12 is a block diagram of a typical smartphone that has been programmed to implement a cough detection apparatus 39. The apparatus 39 includes a processing assembly 3 that accesses an electronic memory 5. The electronic memory 5 includes an operating system 8 such as the Android operating system or the Apple iOS operating system, for example, for execution by the processing assembly 3. The electronic memory 5 also includes cough detection application software product or "App" 6 according to a preferred embodiment of the present invention. The cough detection App 36 includes instructions that are executable by the processing assembly 3 in order for the cough detection apparatus 39 to implement the method of the flowchart of FIG. 5A.

Figure 1:
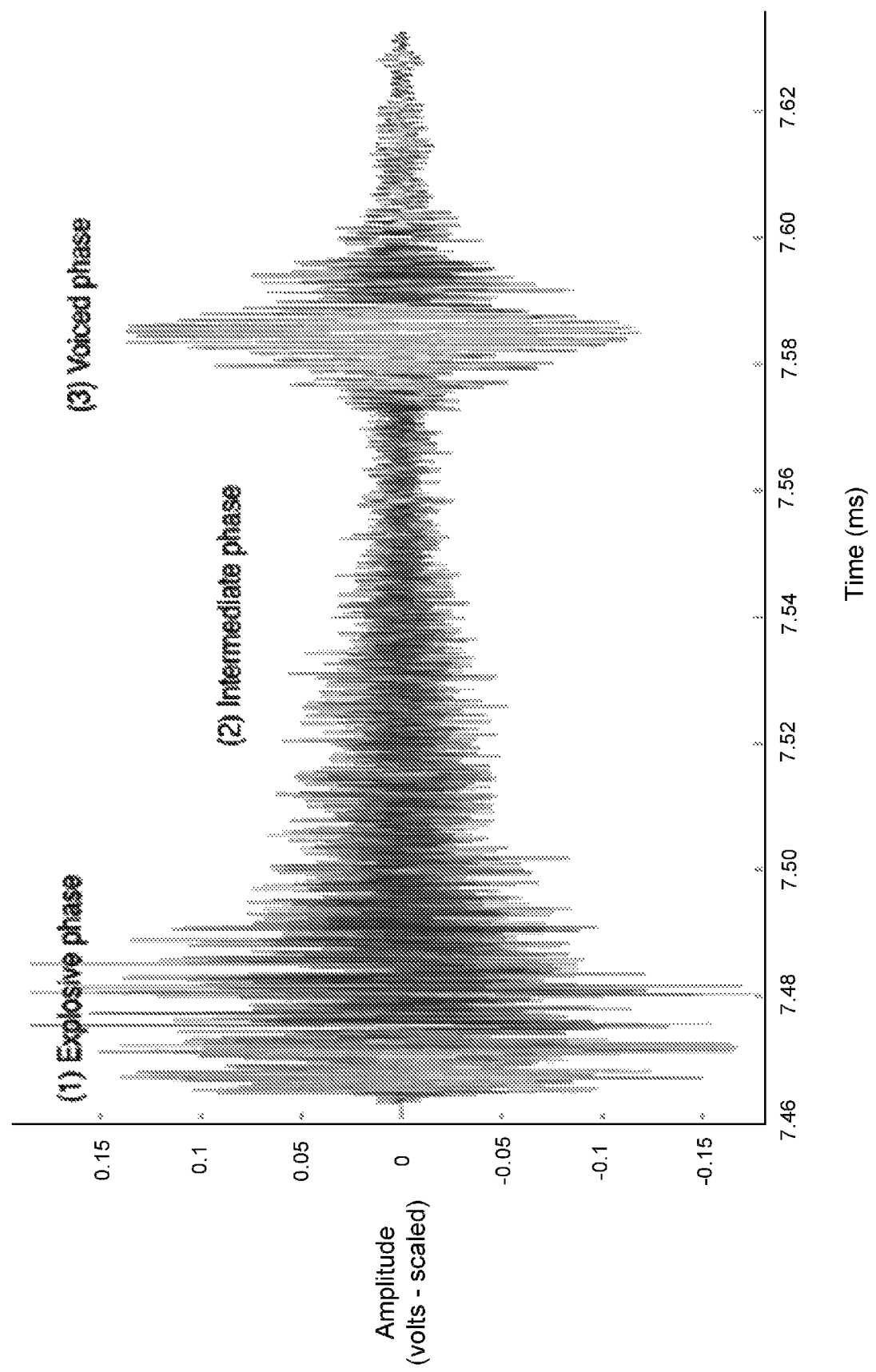
FIG. 1 is waveform of a typical cough sound.

The processing assembly 3 is in data communication with a plurality of peripheral assemblies 9 to 23, as indicated in FIG. 1, via a data bus 7. Consequently, the cough detection apparatus 39 is able to establish data communication with a data communications network 31 via WAN/WLAN assembly 23 and radio frequency antenna 29. In use the apparatus 39 establishes data communication with a remote server 33 from which updates to the App 36 may be downloaded or to which detected cough sounds may be uploaded for diagnosis.

In use a medical care provider operates the cough detection apparatus 39 by executing the cough diagnosis App 36. The App 36 presents a recording screen on LCD Screen 11 which includes a "Start Recording" button via touch screen interface 13. Once the medical care provider has located the cough detection apparatus 39 sufficiently close to the patient the care provider clicks on the "Start Recording" button. Sounds from the patient, including cough sounds are recorded by the microphone 25. Those sounds are filtered and converted into a digital data stream by the audio interface assembly 21. The processing assembly 3, executing the instructions that comprise the cough diagnosis App 36 implements the various functional blocks of the dedicated apparatus 600 of FIG. 6. Upon detecting a cough the processing assembly 3 writes a record of the portion of the recorded sound wave that stores the cough to thereby identify the cough and may operate screen 11 to visually indicate that a cough has been detected to a clinician. The coughs that have thus been identified may be subsequently processed by a diagnostic method to determine if they indicate a disease state of the patient and appropriate therapy provided to the patient, such as antibiotics, hydration and rest. The number of coughs and their positions in the sound wave are then made available for display on the screen 11. Portions of the sound wave containing the detected coughs may also be stored in memory 5 for subsequent diagnostic processing.

Variations and further embodiments of the invention are possible. For example, while neural networks have been used in the preferred embodiment of the invention to classify sounds, other classifiers might instead be used such as decision trees (including bagged or boosted trees). It is also important to note that in the preferred embodiment two classifiers have been used, being TDNN1 615 for the first phase of the cough and TDNN2 617 for the second and third phases of the cough. In other embodiments of the invention three classifiers may be used (one for each individual phase of the cough).

Figure 13:
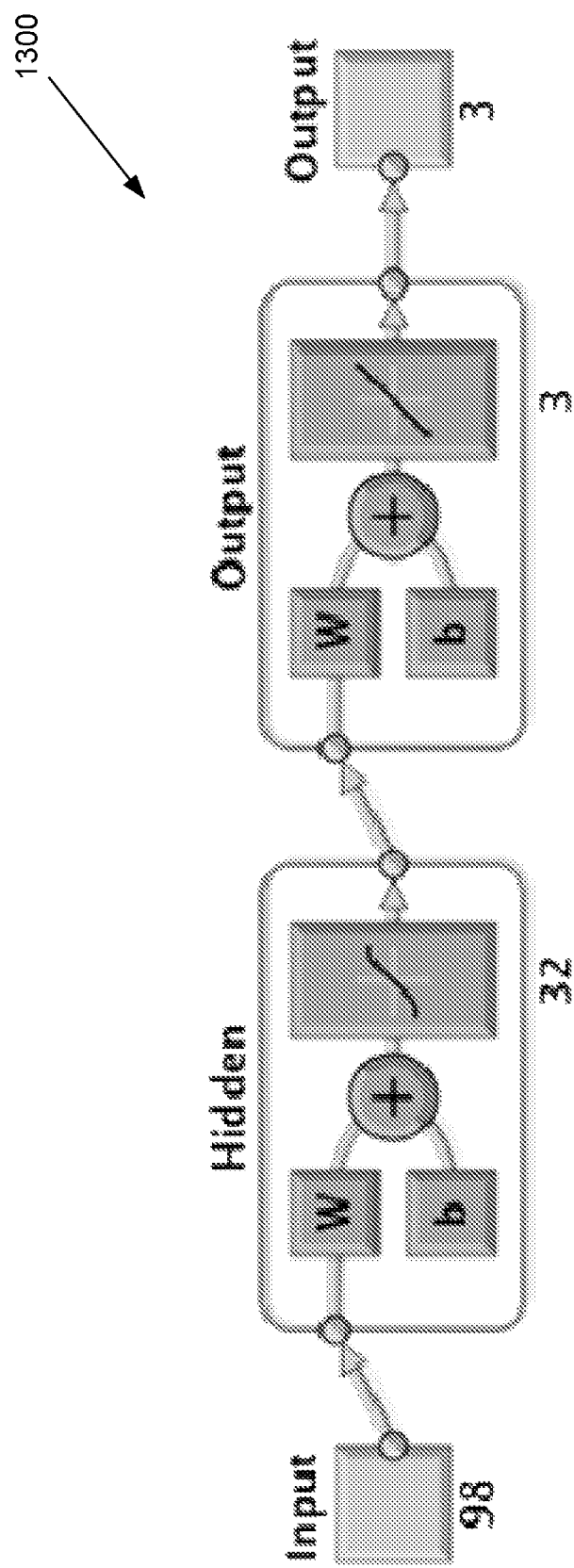
FIG. 13 is a block diagram of the structure of a second "multi-class" classifier according to a second embodiment of the present invention.

In another embodiment of the invention a single multiclass pattern classifier is provided that is trained to process a candidate cough sound and differentiate between the first part and the second part of the cough at the same time is used. FIG. 13 is a diagram of an exemplary neural network 1300 that has been trained to differentiate between the first and second parts of the cough at the one time. It should be noted that the neural net 1300 of FIG. 13 is multi-class in that it generates three outputs, in contrast to the earlier discussed neural net 615 of FIG. 9 which produces a single output.

The neural net 1300 of FIG. 13 is trained to detect three classes for each frame of the audio signal. The three classes are the first cough part, the second cough part or, in the absence of a first cough part and a second cough part, a negative training example. The three output signals from the neural network 1300 correspond to the detection probabilities for each of the three classes. The probabilities for each of the two cough parts can then be used in the same way as the output from the two neural networks of the earlier embodiment of the invention. A cough detector according to the multi-class approach may be implemented using a general hardware platform as for one of the earlier described embodiments of the invention, e.g. the smartphone hardware of FIG. 12.

Figure 14:
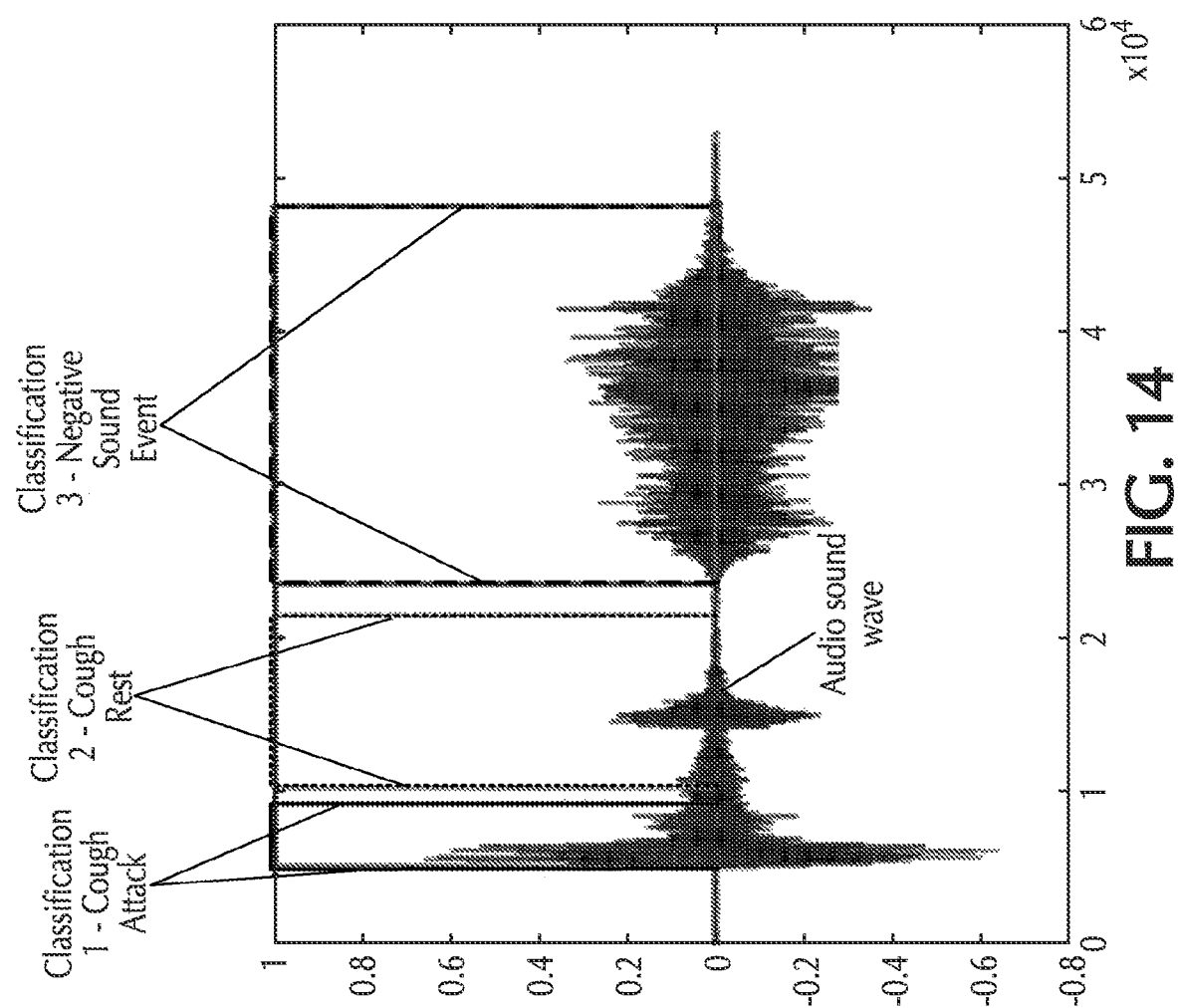
FIG. 14 is a plot of a cough sound waveform indicting portions of the waveform from which features are taken to train the multi-class classifier of FIG. 13.

The training targets for the three classes are illustrated in the plot of FIG. 14. In FIG. 14 the continuous line represents the section of audio features where the cough attack is active (class 1). The dotted line is for the second part of the cough (class 2) and the dashed line represents negative training examples (class 3).

As illustrated in Table 3, the Inventors have found that the performance of the multi-class approach that is illustrated in FIGS. 13 and 14 is slightly worse than the performance of the earlier two neural network embodiment that has been previously discussed.

TABLE 3

Performance Comparison for Different Implementations.

| | Recall (%) | Precision (%) | F1-Score |
|---|---|---|---|
| LW2<br>2 Neural Networks | 80 | 89 | 0.84 |
| LW2<br>2 Tensorflow Networks | 78 | 85 | 0.82 |
| LW2<br>Multi-class approach<br>(One Neural Network) | 76 | 86 | 0.81 |
| LW2<br>Tree Ensembles | 67 | 90 | 0.77 |
| LW2<br>XG Boost | 70 | 84 | 0.76 |

Alternative Models

It is not essential to use a neural network to classify the cough frames in either a 2-model or multi-class model structure. The Inventors have also tested the methods set out herein with several other model types:

Ensembles of decision trees
Gradient boosted trees
Alternative neural network software All of these models achieved similar performance to the original implementation as set out in Table 3.

In compliance with the statute, the invention has been described in language more or less specific to structural or methodical features. The term "comprises" and its variations, such as "comprising" and "comprised of" is used throughout in an inclusive sense and not to the exclusion of any additional features. It is to be understood that the invention is not limited to specific features shown or described since the means herein described herein comprises preferred forms of putting the invention into effect. The invention is, therefore, claimed in any of its forms or modifications within the proper scope of the appended claims appropriately interpreted by those skilled in the art.

Throughout the specification and claims (if present), unless the context requires otherwise, the term "substantially" or "about" will be understood to not be limited to the value for the range qualified by the terms.

Any embodiment of the invention is meant to be illustrative only and is not meant to be limiting to the invention.

The invention claimed is:

1. A method for detecting cough sounds from a sound wave including the steps of:
   acquiring the sound wave in electronic format;
   applying features extracted from the sound wave to at least two electronic pattern classifiers including a first classifier trained to detect an explosive phase of a cough sound and a second classifier trained to detect one or more post-explosive phases of the cough sound, the second classifier being arranged according to a training that is negative in respect of the explosive phase and positive in respect of portions of the cough sound subsequent to the explosive phase; and
   identifying the cough sounds based on outputs from the first classifier and the second classifier.

2. A method according to claim 1, including applying the features extracted from the sound wave to the second classifier only after the first classifier has classified features of the sound wave as an explosive phase of the cough sound.

3. A method according to claim 1, wherein the first classifier is arranged according to a training that is positive in respect of the explosive phase and negative in respect of portions of the cough sound subsequent to the explosive phase.

4. A method according to claim 3, including providing a gap between an end of the explosive phase and commencement of said cough sound subsequent to the explosive phase.

5. A method according to claim 3, wherein the first and second classifiers comprise neural nets having a single hidden layer.

6. A method according to claim 1, wherein the features include features corresponding to mel-frequency cepstral coefficients of the sound wave.

7. A method according to claim 6, wherein the features further include a feature corresponding to log-energy of the sound wave.

8. A method according to claim 1, wherein the first and second classifiers comprise time delay neural nets.

9. An apparatus for detecting cough sounds of a sound wave comprising:
   a digitizing assembly for digitizing output from a transducer for transducing the sound wave;
   a feature extraction assembly in communication with the digitizing assembly for extracting a plurality of features from consecutive segments of the sound wave;
   a first classifier responsive to the feature extraction assembly trained to recognize an explosive phase of a cough sound;
   a second classifier responsive to the feature extraction assembly trained to recognize one or more post-explosive phases of the cough sound;
   first and second comparators for comparing outputs from the first and second classifiers to threshold values for gauging respective detection probability levels of the explosive phase and the post explosive phase; and
   a post-classifier cough identification processor arranged to identify the cough sounds based on outputs from the first classifier and the second classifier.

10. An apparatus according to claim 9, wherein the post-classifier cough identification processor is arranged to respond to an output from the second classifier subsequent to the output from the first classifier indicating detection of the explosive phase of the cough sound.

11. An apparatus according to claim 9, wherein the first classifier and the second classifier comprise first and second neural nets wherein the first neural net is weighted in accordance with positive training to detect the explosive phase and wherein the second neural net is weighted in accordance with positive training to detect the one or more post-explosive phases.

12. An apparatus according to claim 11, wherein the first neural net is further weighted in accordance with positive training in respect of the explosive phase and negative training in respect of the post-explosive phases.

13. An apparatus according to claim 11, wherein the second neural net is further weighted in accordance with negative training in respect of the explosive phase and positive training in respect of the post-explosive phases.

14. An apparatus according to claim 9 comprising a feature extraction assembly arranged to extract mel-frequency cepstral coefficients (MFCCs) from the sound wave.

15. An apparatus according to claim 14, wherein the feature extraction assembly is arranged to extract MFCCs including a zeroth order MFCC.

16. An apparatus according to claim 14, wherein the feature extraction assembly is further arranged to extract a log-energy feature of the sound wave.

17. An apparatus according to claim 9, wherein the cough identification processor is responsive to the comparators for identifying the cough sounds.

18. An apparatus according to claim 9, wherein the cough sound identifier includes an RMS power estimator for estimating the RMS power of segments of the sound wave wherein the cough identification processor is arranged to identify the cough sounds taking into account output from the RMS power estimator.

19. An apparatus according to claim 9 comprising a cough flagger assembly that is responsive to the post-cough identification processor, wherein the cough flagger assembly is arranged to record portions of the sound wave identified to contain cough sounds.

20. An apparatus according to claim 11, wherein the first and second neural nets comprise time delay neural nets for processing a sequence of time delayed feature vectors emanating from the feature extraction assembly.

* * * * *